(12) United States Patent
Muzzarelli et al.

(10) Patent No.: US 8,383,157 B2
(45) Date of Patent: Feb. 26, 2013

(54) PREPARATION OF CHITIN AND DERIVATIVES THEREOF FOR COSMETIC AND THERAPEUTIC USE

(75) Inventors: Corrado Muzzarelli, Ancone (IT); Pierfrancesco Morganti, Aprilia (IT)

(73) Assignee: Mavi Sud S.r.l., Aprilia LT (IT)

( * ) Notice: Subject to any disclaimer, the term of this patent is extended or adjusted under 35 U.S.C. 154(b) by 463 days.

(21) Appl. No.: 11/666,427

(22) PCT Filed: Nov. 2, 2005

(86) PCT No.: PCT/IB2005/053576
§ 371 (c)(1), (2), (4) Date: Apr. 27, 2007

(87) PCT Pub. No.: WO2006/048829
PCT Pub. Date: May 11, 2006

(65) Prior Publication Data
US 2008/0118563 A1   May 22, 2008

(30) Foreign Application Priority Data
Nov. 2, 2004   (IT) .............................. RM2004A0539

(51) Int. Cl.
*A61K 9/14*   (2006.01)
*A61M 5/00*   (2006.01)
*A61M 11/00*   (2006.01)
*A61M 35/00*   (2006.01)
*A01N 43/04*   (2006.01)
*C08B 37/08*   (2006.01)

(52) U.S. Cl. ..................... 424/488; 128/200.14; 514/55; 536/20; 604/187; 604/289

(58) Field of Classification Search .................. None
See application file for complete search history.

(56) References Cited

U.S. PATENT DOCUMENTS

| 4,029,727 | A  | * | 6/1977 | Austin et al. ................. 264/186 |
| 6,602,994 | B1 |   | 8/2003 | Cash et al. |
| 6,753,014 | B1 | * | 6/2004 | Sjoblom ....................... 424/489 |
| 2002/0173213 | A1 | * | 11/2002 | Chu et al. .................... 442/414 |
| 2003/0049290 | A1 | * | 3/2003 | Jha et al. ..................... 424/401 |
| 2003/0206949 | A1 | * | 11/2003 | Parikh et al. ................. 424/465 |

FOREIGN PATENT DOCUMENTS
WO   2006/048829 A3   9/2006

OTHER PUBLICATIONS

Lee, S.B., Y.M. Lee, K.W. Song, and M.H. Park. 2003. Preparation and Properties of Polyelectrolyte Complex Sponges Composed of Hyaluronic Acid and Chitosan and Their Biological Behaviors. Journal of Applied Polymer Science, vol. 90: 925-932.*
Ohshima, Y., K. Nishino, Y. Yonekura, S. Kishimoto, and S. Wakabayashi. 1987. Clinical Application of Chitin Non-Woven Fabric as Wound Dressing. European Journal of Plastic Surgery, vol. 10: 66-69.*
Li, J., J.F. Revol, E. Naranjo, and R.H. Marchessault. 1996. Effect of electrostatic interaction on phase separation behavior of chitin crystallite suspensions. International Journal of Biological Macromolecules. 18: 177-187.*
International Search Report for PCT/IB2005/053576, Jul. 3, 2006.
International Preliminary Report on Patentability for PCT/IB2005/053576, Oct. 17, 2006.
Choi et al. "Studies on gelatin-based sponges. Part III: A comparative study of cross-linked gelatin/alginate, gelatin/hyaluronate and chitosan/hyaluronate sponges and their application as a wound dressing in full-thickness skin defect of rat" Journal of Materials Science, vol. 12, No. 1, pp. 67-73, 2001.
Hirano et al. "The preparation and application of functional fibres from crab shell chitin" Journal of Biotechnology, vol. 70, No. 1-3, pp. 373-377, Apr. 30, 1999.
Hirano et al. "Release of glycosaminoglycans in physiological saline and water by wet-spun chitin-acid glycosaminoglycan fibres" Journal of Biomedical Materials Research, vol. 56, No. 4, pp. 556-561, Sep. 2001.
Kim et al. "Synthesis and characteristics of polyelectrolyte complexes composed of chitosan and hyaluronic acid" Journal of Applied Polymer Science, vol. 91, pp. 2908-2913, Jul. 30, 2003.
Lee et al. "Preparation and properties of polyelectrolyte complex sponges compose of hyaluronic acid and chitosan and their biological behaviours" Journal of Applied Polymer Science, vol. 90, No. 4, pp. 925-932, Oct. 24, 2003.
Muzzarelli et al. "Spray-drying of solutions containing chitosan together with polyuronans and characterisation of the microspheres" Carbohydrate Polymers, vol. 57, No. 1, pp. 73-82, Aug. 12, 2004.
Ohshima et al. "Clinical application of chitin non-woven fabric as wound dressing" European Journal of Plastic Surgery, vol. 10, pp. 66-69, 1987.

* cited by examiner

*Primary Examiner* — Carlos Azpuru
*Assistant Examiner* — David Browe
(74) *Attorney, Agent, or Firm* — Nixon & Vanderhye P.C.

(57) ABSTRACT

The invention relates to novel chitin derivatives and their use in medical treatments of plastic surgery, dermocosmesis and therapy, in particular it relates to natural chitin derivatives, like chitin in nanofibrillar form, oxychitin and other chemical derivatives of chitin, chitosan-hyaluronate and associations for use as subcutaneous fillers or skin protectants.

8 Claims, No Drawings

PREPARATION OF CHITIN AND DERIVATIVES THEREOF FOR COSMETIC AND THERAPEUTIC USE

This application is a U.S. national stage of International Patent Application No. PCT/IB2005/053576, filed 2 Nov. 2005, which designated the U.S. and claims priority benefit of IT RM2004A000539, filed 2 Nov. 2004; the entire contents of each of which are hereby incorporated by reference.

TECHNICAL FIELD OF THE INVENTION

The invention relates to novel chitin derivatives and their use in medical treatments of plastic surgery, dermocosmesis and therapy.

STATE OF THE ART

Chitin

Chitin is secreted in vivo as a rapidly crystallizing amorphous material with a characteristic fibrillar structure widely studied and described. The secretory organs called chitosomes contain, besides chitin synthetase, various other enzymes presiding to the transformations required to achieve the polysaccharide fibril. Said fibril is then linked to proteins and joins a system in which chitin is immersed in proteins or in glucans and forms support structures of animals and fungi, respectively.

Studies of Revol J F et al. (1996) demonstrated that suitable chemical (boiling in HCl) and physical (sonication) treatments of crab (shell) alpha-chitin lead to the isolation of chitin nanofibrils (chitin whiskers) in aqueous suspension. These form polydispersed systems having average dimensions of 8 nm in width and 200 nm in length, of rectangular section, and exhibit a certain tendency to form aggregates of 2 or 3 nanofibrils: in practice, hydrochloric acid removes the scarcely crystalline components of the fibers, freeing the nanofibrils.

Water evaporation from the nanofibril suspensions yields films exhibiting arched patterns that indicate a chiral nematic order. These phenomena are present also in collagen and in cellulose (Samir et al., 2001) in which analogous nanofibrils may be isolated.

In view of their structural perfection and small width (generally ranging from 2.8 to 25 nm) nanofibrils are endowed with a peculiar geometric regularity and exhibit extremely high mechanical resistance. In fact, nanofibrils constitute biological tissues intended for huge efforts, such as the pre-alar joints of *Locusta migratoria*, the rear leg tendon of *Schistocerca gregaria*, and the crab's claw tendon.

For this reason, actual research tend to take advantage of mechanical characteristics, by proposing alpha-chitin nanofibrils as reinforcing materials for widely used natural and synthetic polymers. For instance, Nair and Dufresne (2003) propose to reinforce natural rubber with nanofibrils, whereas Lu et al. (2004) and Paillet and Dufresne, (2001) add nanofibrils to thermoplastics obtained from soy proteins, or other polymers like poly(caprolactone) (Morin and Dufresne, 2002). Nge et al. (2003) described polyacrylates reinforced with chitin nanofibrils. There have been described chemical modifications of chitin in the form of nanofibrils, in particular sulfonation (Li et al., 1997).

According to current literature, the technical applications of chitin nanofibrils tend to follow the example of natural systems (nanofibrils immersed in protein or polysaccharide matrices) reinforcing low-modulus matrices with high-modulus fibrils, i.e. taking advantage of the exceptional mechanical characteristics of chitin nanofibrils.

Apparently, current research on chitin nanofibrils has so far ignored their interesting biochemical characteristics. To date, these characteristics have not been adequately exploited in the dermal surgery field, in plastic surgery, in the cutaneous and subcutaneous administration of biological filler materials (fillers) for aesthetical, cosmetic and therapeutical (medical) purposes.

Common knowledge indicates that pure chitin, in the form of non-woven fabric or yarn, is highly biocompatible with human tissues, as amply demonstrated by researches on wound medication (Ohshima et al., 1987) and by the commercial availability of chitin-based medication products in Far Eastern countries; (II) is not recognized as an extraneous body; (III) is biodegradable, as already highlighted by works with films of chitin implanted in rat's back; it has been used as suture thread in rat's muscle, where it has been reabsorbed in 4 months (Nakajima et al., 1986), and in a very wide range of case histories, comprising surgery in which the chitin flake was sutured inside the organism as a filler (Okamoto et al., 1993); is slowly readsorbable also in human tissues by means of lysozime, acting on chitin tel quel and on up to 30% deacetylated chitins (Tomihata and Ikada, 1997); (IV) influences collagen's proline-hydroxyproline ratio; (V) fosters proliferation of fibroblasts, collagen producers (Shibata et al., 1997); (VI) is not antigenic, instead fostering the organism's immunologic response; (VII) is a haemostatic agent (Kulling et al., 1999); (VIII) has been administered intravenously as a thin-particle suspension causing fagocytosis by macrophages.

Pure chitin exhibits certain adverse characteristics limiting its application, such as, in particular, insolubility, hardness, crystallinity, and difficult handling of the various chitins.

In order to avoid these unfavorable characteristics, in the past it has been proposed the use of colloidal chitin, which is prepared with hydrochloric acid under cold conditions. However, the resulting colloidal chitin suspension is turbid due to the strong aggregation and the variable size of the particles (Jeuniaux, 1958).

Hyaluronic Acid

To date, the substance preferred in plastic surgery to swell up lips or smooth out wrinkles is hyaluronic acid in physiological solution. This polysaccharide has the capability of structuring water, thanks to its very high molecular weight, hydrophilicity and configuration. Its use is simple, yet by its nature it is prone to an easy and rapid in vivo enzymatic hydrolisis by means of hyaluronidase and other hydrolases. Therefore, the effect exerted on tissues following the injection lasts a few days and the treatment has to be repeated frequently. Other unfavorable aspects of hyaluronic acid may be related to its animal origin.

However, it is known that hyaluronic acid, as a polyanion, is capable of forming polyelectrolyte complexes with chitosan, and that these complexes can be shaped as microspheres (Muzzarelli et al., 2004). Said complexes are characterized by lesser sensitivity to endogenous hydrolytic enzymes and may be intended as original fillers. However, an impediment to the use of said complexes ensues from the strongly hydrophilic nature of both components, causing them to swell in an aqueous environment; the swelling impedes a subcutaneous injection, as the microspheres become of sizes such that they mutually hinder themselves during in-needle transit. Therefore, overall the chitin derivatives known to date are not suitable for use as filler in plastic surgery or, more generally, in dermatology, due to a range of problems all stemming from the tendency of these substances, or of complexes comprising them, to aggregate or swell when placed in an aqueous medium.

This phenomenon, typical of pure chitin in the known form of colloidal chitin, or of chitosan-hyaluronate, decreases both the feasibility and the effectiveness of use of such derivatives. In fact, aggregates make it extremely difficult, if not impossible, the flow of the aqueous suspension of said substances through common needles used for dermocosmetic surgery, as well as through any device for topical on-skin application, such as spray or nebulizers or pencils. Moreover, a product containing heterogeneous aggregates, when applied subcutaneously or in the form of a thin cutaneous film, does not exhibit the characteristics of homogeneity required to assure the optimal result.

Scope of the present invention is to offer a solution to these problems.

SUMMARY OF THE INVENTION

The invention provides novel means to solve the problem, shared by all chitin derivatives, of the forming of large-sized particles in suspension.

It has surprisingly been observed by the present inventors that when pure chitin is subjected to a process of preparing nanofibrils and used in this form, the nanofibrils do not aggregate appreciably and form stable suspensions, their advantage being that of flowing without difficulty through a G30 needle, i.e. the needle preferred for injecting cutaneous fillers in the treatment of facial wrinkles and other blemishes or through devices for on-skin spray application.

Likewise, it has been observed that in the case of chitosan/hyaluronic acid complexes the swelling of the microspheres composed of said complex may be eliminated if the microspheres are cross-linked with suitable chemical reagents.

However, these interventions per se do not completely solve the problem of the aggregation of large-sized particles. In fact, both the nanofibrillar chitin and the cross-linked chitosan-hyaluronate, as well as any other chitin derivative, when reconstituted in a liquid suspension, after lyophilization or other form of dehydration, likewise tend, albeit less markedly, to produce large-sized aggregates.

This additional problem has effectively been solved by the inventors with addition to the composition of chitin or derivatives thereof of a plasticizer enabling the quick reconstitution of the dehydrated mass into perfectly homogeneous suspensions.

Hence, object of the present invention is a medical-surgical composition, comprising, in a pharmaceutically acceptable excipient, a natural chitin derivative selected among nanofibrillar chitin, chemical derivatives thereof, chitosan glycolate and cross-linked chitosan-hyaluronate.

A second object of the invention is the medical-surgical composition comprising a plasticizer and, optionally, further substances such as amino saccharide derivatives selected among chemically modified chitin, hyaluronic acid, oxychitin and chitosan, chitosan glycolate and agents apt to prevent infections. Further object of the invention are single-use or multi-use syringes, or vials containing the composition in lyophilized form, as well as containers containing the liquid suspension and equipped with a device for topical application of the suspension, e.g. spray or pencils.

Other objects of the invention are chitin nanofibrils, optionally dispersed in a plasticizer, or cross-linked chitosan-hyaluronate microspheres, optionally dispersed in a plasticizer, for use in a medical-surgical treatment, in particular for intradermal-epidermal or hypodermic (subcutaneous) administration in a plastic surgery or dermocosmesis treatment or by topical administration in the protective or curative treatment of skin abrasions, wounds or burns.

Lastly, object of the invention are also methods of preparing the compositions and methods of preparing syringes, vials or containers containing the liquid or solid suspension.

DETAILED DESCRIPTION OF THE INVENTION

The compositions of the invention comprise, as main constituent, a natural chitin derivative. The starting product for the compounds of the invention is crustacean chitin, for instance commercially available crab alpha-chitin of medical-pharmaceutical grade. Other types of chitin may be used as well.

Chitin nanofibrils may be produced according to known methods by chemical treatment of chitin with acids under boiling conditions, e.g. with HCl, or by physical treatment, e.g. by sonication. It has been observed that chitin nanofibrils, though sensitive to the hydrolytic action of the in vivo lysozime, slow down its action as they are highly regular structures, less easily attackable than powders, microspheres and other physical forms. For this reason, nanofibrillar chitin, isolated in sterile environment and suitably treated and packaged, is susceptible of being injected subcutaneously for dermocosmesis treatments whose effects last longer than the traditional ones making use of hyaluronic acid.

Other useful derivatives of natural chitin are chitins chemically treated in order to modify their chemico-physical behavior, e.g. through sulfonation as described by Li et al. (1997), oxychitin or chitosan, which are variously modified forms of chitin. Chitosan is preferably used as salt of glycolic acid, i.e. chitosan glycolate, or in a polyelectrolyte complex with hyaluronic acid in the form of microspheres, as described by Muzzarelli et al (2004). The tendency to swell typical of these complexes is eliminated, according to the invention, through cross-linking at their surface. The cross-linking is conducted in an organic environment, e.g. butanol, by means of suitable cross-linking agents such as ascorbyl palmitate, epichlorohydrin, dicyclohexylcarbodiimide or other known cross-linkers.

The compositions of the invention may comprise plural derivatives of chitin. In one of the embodiments of the invention the chitin nanofibrils may be coupled with hyaluronic acid, i.e. be suspended in a solution of said acid having a concentration of 0.3-2.5%, e.g. of 0.5%. Suitably, the hyaluronic acid will be dissolved in physiological solution (0.9% NaCl) to prevent the former from functioning as aggregant of the chitin nanofibrils. In fact, the latter exhibit sporadic positive charges due to a somewhat small chitin deacetylation rate (usually 0.10) common to all chitins of animal origin. Hyaluronic acid, capable of forming polyelectrolyte complexes, would aggregate the chitin nanofibrils, but for the ionic force of the physiological solution, which with the charges of the sodium and chloride ions prevents this. Therefore, the chitin nanofibrils may be suspended in solutions of hyaluronic acid and NaCl, optionally in the presence of a plasticizer.

In other embodiments of the invention, the nanofibrillar chitin is associated to chitosan, chitosan glycolate, chitosan-hyaluronate, oxychitin or to the oxychitin-hyaluronic acid complex. Also the oxychitin complexes are usually in the form of microspheres, cross-linked when needed.

The purpose of the plasticizer optionally contained by the compositions of the invention is that of facilitating the reconstitution of the suspension in aqueous solvent of the nanofibrils or chitin microspheres or derivatives thereof, above all after drying or lyophilizing. Suitable plasticizers are usually polyols like glycerin or glycerol, sorbitol, mannitol, or neutral salts of hydroxymethylglycinate, such as neutral sodium hydroxymethylglycinate, or any other equivalent substance.

Though the compositions of the invention are usually pure, sterile and apyrogenic, an essential requirement for parenteral-subcutaneous administration, these may nevertheless comprise agents apt to prevent infections, such as disinfectants or antibacterials. For example, for the treatment of superficial lesions through spray application of nanofibrillar chitin, intended to form an absorbable protective layer onto the wound or abrasion, there may be used disinfectant substances such as colloidal silver or silver sulfadiazine.

The compositions of the invention may be produced by direct suspension of nanofibrillar chitin or of other chitin derivatives, optionally associated to other amino saccharides or anti-infectives, in water or sterile and apyrogenic aqueous solvent compatible with human tissues. The suspensions so obtained are suitable for immediate use, e.g., by subcutaneous injection or topical application. Alternatively, the suspensions may be brought into a form more suitable for storage, e.g. through dehydration or lyophilization. In this latter case the composition will preferably contain also the plasticizer in order to facilitate the reconstitution, before use, of a homogeneous suspension through addition of a minimal amount of liquid medium and gentle stirring. It is important to note that the addition of a plasticizer, e.g. glycerol, to the suspension to be lyophilized leads to the yielding of a lyophilized mass having the characteristics not of the dry solid, but rather of a semisolid mass, e.g. a paste, keeping a certain moisture percentage.

The compositions of the invention, in the form of suspension, may be distributed in predefined amounts for single-use or multi-use into syringes for hypodermic injection. In this case, the composition may subsequently be lyophilized directly in-syringe and stored or packaged in this form.

Alternatively, the suspension may be distributed in a predefined amount into vials suitable for lyophilization, and stored or packaged in this form. In a further embodiment of the invention, the suspension is distributed in liquid form into containers equipped with devices for topical on-skin application, e.g. in spray canisters, nebulizers, pencils, brushes or other usual means capable of depositing on-skin a thin film, which, after drying, generates a thin film of material, protective and absorbable over time, to protect wounds, abrasions, irritations or burns.

Moreover, the fact that chitin nanofibrils possess weak cationic character, something however not previously described in literature, enables to adsorb them on spongy surfaces or on film, or on yarns having anionic character, e.g. modified cellulose like carboxymethyl cellulose, or polyacrylate or natural or synthetic fabrics suitable for dermocosmesis treatment by face masks or for prevention of dermatological allergies. These articles differ from those described in the prior art, as the former do not incorporate chitin nanofibrils thereinside, rather having the surface covered with nanofibrils.

The compositions of the invention find application in the cosmetic surgery field, in particular in the dermocosmesis field, as cutaneous fillers for the treatment of wrinkles and other cutaneous irregularities and blemishes through subcutaneous hypodermic injection. Instruments for the carrying out of said treatments are the known hypodermic syringes having G30-size needles. Preferably, the treatment is conducted with the syringes according to the invention, already containing a defined dose of composition in lyophilized form and easily reconstituted in suspension immediately before use.

A second application is the purely therapeutic one, in the treatment of protecting irritated, wounded, abraded or burned skin, and in the treatment for supporting and stimulating hemostasis, tissue healing and regeneration processes. In such an application, the composition in the form of liquid suspension is distributed on-skin as a thin liquid film deposited with suitable devices disclosed above. After evaporation, the liquid film results in a thin protective film, of a material compatible with tissues and capable of being absorbed gradually and concomitantly to the healing up of the wound. In case of burns, or of other traumas in which wide body areas are involved, the application of the composition through spray dispenser is the most effective. Pencils equipped with a ball-shaped dispenser or the like or brushes may be useful for application on small-size alterations.

Lastly, depending on the type of chitin derivative used in the application, such a derivative will be in a pure form or in a plasticized form.

Hereinafter the invention will be described by means of examples, having a merely exemplary and non-limiting purpose.

Example 1

Chitin Nanofibrils Preparation

A 3N HCl solution (400 ml) is prepared in a 500 ml-flask with reflux, and 5 g crustacean (preferably crab) chitin of medical-pharmaceutical grade are suspended therein. The suspension is boiled 90 min, then left to cool. The highly turbid supernatant is centrifuged at 4000 rpm for 10 min, decanted, and the acid supernatant is discarded and replaced through two successive dilution cycles with sterile distilled water and centrifugation: accordingly, pH rises to at least 4. After a third cycle the supernatant does not clarify as before anymore, as chitin nanofibrils have formed in the colloidal suspension. pH is of about 5. This supernatant (suspension of nanofibrils) is susceptible of passing through the G30 needle. The chitin nanofibrils thus obtained may be recovered from the colloidal suspension through ultracentrifugation from 12.000 to 20.000 rpm.

However, the sediment from the third centrifugation contains a prevailing fraction of chitin in the form of nanofibrils: when carefully stirred, it partially resuspends so that a good amount of nanofibrils is recovered, which can likewise be precipitated through centrifugation. Overall, the yield is of about 30-40%. Alternatively, the suspensions of nanofibrils are charged with highly pure glycerol, then frozen and lyophilized. It is yielded a paste of nanofibrils in glycerol which is stored without problems and easily redispersed with a minimum amount of water.

Example 2

Formulation of Chitin Nanofibrils with Neutral Sodium Hydroxymethylglycinate

Sodium hydroxymethylglycinate (50%) provided by Mavi-Sud is an antimicrobial useful for cosmetic formulations, produced by Sutton, N.J., USA, CAS No 70161-44-3. 0.3 M HCl (5.5 ml) is added to 10 ml sodium hydroxymethylglycinate (50%) to adjust its pH, which from 11 becomes 7 (neutral hydroxymethylglycinate). Chitosan powder (2 g) is wetted in 30 ml water, and glycolic acid (912 mg) is added. This solution is divided into 4 aliquots of about 7.5 g (each one containing 0.5 g chitosan, 7.5 ml water and 228 mg glycolic acid).

1) To the first aliquot of chitosan glycolate it is added neutral hydroxymethylglycinate (85 microliters) prediluted in water (2.5 ml); final pH of 4.5.

2) To the second aliquot it is added neutral hydroxymethylglycinate (170 microliters) prediluted in water (2.5 ml); final pH of 4.8.

3) To the third aliquot it is added neutral hydroxymethylglycinate (255 microliters) prediluted in water (2.5 ml); final pH of 5.0.

4) To the third aliquot there are added 100 mg chitin nanofibrils presonicated in water (2.5 ml), then neutral hydroxymethylglycinate (85 microliters); final pH of 4.5.

It was observed that aliquots 1 and 4 gelled rapidly and achieved the same consistency; no difficulties were experienced in dispersing the nanofibrils in the presence of chitosan glycolate, and no undesirable effects were observed at +2 weeks.

Aliquots 2 and 3 achieved higher consistency with respect to 1 and 4. However, 1 and 4 contained hydroxymethylglycinate in a concentration recommended for antimicrobial activity, whereas the others contained an excess thereof.

Lastly, it was observed that neutral hydroxymethylglycinate has the ability to gel chitosan glycolate solutions via an unknown mechanism, with no local precipitation of the chitosan (not even transitorily). According to the producer, neutral or slightly acid hydroxymethylglycinate has the same antimicrobial abilities of the original one at a pH of 11.

The gel under 4) is advisable for a ready administration of chitosan and chitin to wounds, even bleeding ones, to induce hemostasis and regeneration of injured tissues.

Example 3

Injectable Nanofibrils Presentation

The suspension containing the preferred amount of glycerol-plasticized nanofibrils is introduced into a syringe; this is introduced into a lyophilizer and then packaged. The syringe, at the moment of use, is equipped with a G30 needle from which physiological solution in the preferred amount is sucked. To redisperse the paste of nanofibrils and glycerol, weak vibrations are manually given to the vertically held syringe, obtaining in less than 4 minutes a milky suspension of nanofibrils, easily injectable.

Example 4

Chitosan-Hyaluronate Cross-Linking

The microspheres of chitosan-hyaluronate were suspended in butanol; subsequently, ascorbyl palmitate was added, in a 14:1 weight ratio with respect to the microspheres. The suspension was agitated at 50° C. for 15 hours, concomitantly blowing in air; filtration was performed on a 0.22-micron filter. The filtrate was washed with two aliquots of butanol to eliminate ascorbyl palmitate in excess. The cross-linked microspheres were dispersed in glycerol as plasticizer, and introduced in single-use syringes in the desired amount. By sucking physiological solution into the syringe, they soon disperse and are injectable by G30 needle.

BIBLIOGRAPHY ON NANOFIBRILS

Revol J F, Li J, Godbout L, Orts W J, Marchessault R H, Chitin crystallite suspensions in water. Advances in Chitin Sciences, Domard A, Jeuniaux C, Muzzarelli R A A, Roberts G, eds. Andre, Lyon, p 355, 1996.

Paillet M, Dufresne A. Chitin nanofibrils reinforced thermoplastic nanocomposites. Macromolecules 34, 6527-6530, 2001.

Lu Y, Weng L, Zhang L. Morphology and properties of soy protein isolate thermoplastic reinforced with chitin nanofibrils. Biomacromolecules 5, 1046-1051, 2004.

Nair K G, Dufresne A. Crab shell chitin nanofibrils reinforced natural rubber nanocomposites. 1. Processing and swelling behaviour. Biomacromolecules 4, 657-665, 2003.

Nair K G, Dufresne A. Crab shell chitin nanofibrils reinforced natural rubber nanocomposites. 2. Mechanical behaviour. Biomacromolecules, 4, 666-674, 2003.

Nair K G, Dufresne A. Crab shell chitin nanofibrils reinforced natural rubber nanocomposites. 3. Effect of chemical modification. Biomacromolecules 4, 1835-1842, 2003.

Samir M A S A, Alloin F. Sanchez J Y, Kissi N E, Dufresne A. Preparation of cellulose nanofibrils reinforced nanocomposites from an organic medium suspension. Macromolecules 37, 1386-1393, 2004.

Morin A, Dufresne A. Nanocomposites of chitin nanofibrils from Riftia tubes and poly(caprolactone). Macromolecules 35 2190-2199.

Li J, Revol J F, Marchessault R H. Effect of sulfonation on the colloidal and liquid crystal behaviour of chitin crystallites. Journal of Colloid and interface science 192, 447-457, 1997.

Nge T T, Hori N, Takemura A, Ono H, Kimura T. Liquid crystalline chitin/poly(acrylic acid) composite. Journal of Polymer Science Part B Polymer Physics 41, 711-714, 2003.

C. Muzzarelli, V. Stanic, L. Gobbi, G. Tosi and R. A. A. Muzzarelli, Spray-drying of solutions containing chitosan together with polyuronans, and characterization of the microspheres. Carbohydrate Polymers, 57, 73-82 (2004).

Bibliography on In Vivo Chitin Implants

Tomihata K, Ikada Y. In vitro and in vivo degradation of films of chitin and its deacetylated derivatives. Biomaterials, 18, 567-575, 1997.

Shibata Y, Foster La, Metzfer W J, Myrvik Q N. Alveolar macrophage priming by intravenous administration of chitin particles in mice. Infection and Immunity 65, 1734-1741, 1997.

Okamoto Y, Minami S, Matsuhashi A, Sashiwa H, Saimoto H, Shigemasa Y, Tanigawa T, Tanaka Y, Tokura S. Application of polymeric N-acetylglucosamine (chitin) to veterinary practice. Journal of Veterinary Therapeutic Science 55, 734-747, 1993.

Ohshima Y, Nishino K, Yonekura Y, Kishimoto S, Wakabayashi S. Clinical application of chitin non-woven fabric as wound dressing. European Journal of Plastic Surgery 10, 66-69, 1987.

Bibliography on Chitosan with Hyaluronic Acid

Kim S J, Shin S R, Lee K B, Park Y D, Kim S I. Synthesis and characteristics of polyelectrolyte complexes composed of chitosan and hyaluronic acid. Journal of Applied Polymer Science 91, 2908-2913, 2004.

Lapcik L Jr, Lapcik L, De Smedt S, Desmeester J, Chabrecek P. Hyaluronan: preparation, structure, properties and applications. Chemical Reviews 98, 2664-2684, 1998.

The invention claimed is:

1. A homogeneous chitin suspension consisting of nanofibrillar chitin, plasticizer, and pharmaceutically acceptable excipients; wherein said plasticizer is a polyol; and said composition, when resuspended with an aqueous solvent after dehydration, reconstitutes into a homogeneous suspension.

2. A homogeneous chitin suspension consisting of nanofibrillar chitin, plasticizer, amino saccharide derivative, and pharmaceutically acceptable excipients; wherein said plasticizer is a polyol; said amino saccharide derivative is selected from the group consisting of hyaluronic acid, oxychitin, and chitosan; and said composition, when resuspended with an aqueous solvent after dehydration, reconstitutes into a homogeneous suspension.

3. A homogeneous chitin suspension consisting of nanofibrillar chitin, plasticizer, chitosan glycolate, neutral hydroxymethylglycinate, and pharmaceutically acceptable excipients; wherein said plasticizer is a polyol; and said composition, when resuspended with an aqueous solvent after dehydration, reconstitutes into a homogeneous suspension.

4. A homogeneous chitin suspension consisting of nanofibrillar chitin, plasticizer, a disinfectant or antibacterial agent, and pharmaceutically acceptable excipients; wherein said plasticizer is a polyol; and said composition, when resuspended with an aqueous solvent after dehydration, reconstitutes into a homogeneous suspension.

5. The homogeneous chitin suspension according to claim 1, wherein said polyol is selected from the group consisting of glycerol, sorbitol, mannitol, and hydroxymethylglycinate.

6. The homogeneous chitin suspension according to claim 2, wherein said polyol is selected from the group consisting of glycerol, sorbitol, mannitol, and hydroxymethylglycinate.

7. The homogeneous chitin suspension according to claim 3, wherein said polyol is selected from the group consisting of glycerol, sorbitol, mannitol, and hydroxymethylglycinate.

8. The homogeneous chitin suspension according to claim 4, wherein said polyol is selected from the group consisting of glycerol, sorbitol, mannitol, and hydroxymethylglycinate.

* * * * *

UNITED STATES PATENT AND TRADEMARK OFFICE
CERTIFICATE OF CORRECTION

PATENT NO. : 8,383,157 B2
APPLICATION NO. : 11/666427
DATED : February 26, 2013
INVENTOR(S) : Muzzarelli et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 574 days.

Signed and Sealed this

First Day of September, 2015

Michelle K. Lee
*Director of the United States Patent and Trademark Office*